US010228326B2

(12) United States Patent
Ootani et al.

(10) Patent No.: US 10,228,326 B2
(45) Date of Patent: Mar. 12, 2019

(54) IMMUNOASSAY METHOD UTILIZING SURFACE PLASMON

(71) Applicant: Konica Minolta, Inc., Chiyoda-ku, Tokyo (JP)

(72) Inventors: Makiko Ootani, Tokyo (JP); Takatoshi Kaya, Inagi (JP)

(73) Assignee: KONICA MINOLTA, INC., Tokyo (JP)

(*) Notice: Subject to any disclaimer, the term of this patent is extended or adjusted under 35 U.S.C. 154(b) by 486 days.

(21) Appl. No.: 14/433,230

(22) PCT Filed: Sep. 10, 2013

(86) PCT No.: PCT/JP2013/074399
§ 371 (c)(1),
(2) Date: Apr. 2, 2015

(87) PCT Pub. No.: WO2014/054389
PCT Pub. Date: Apr. 10, 2014

(65) Prior Publication Data
US 2015/0260654 A1 Sep. 17, 2015

(30) Foreign Application Priority Data
Oct. 3, 2012 (JP) .................... 2012-221362

(51) Int. Cl.
G01N 21/552 (2014.01)
G01N 21/64 (2006.01)
(Continued)

(52) U.S. Cl.
CPC ....... G01N 21/6428 (2013.01); G01N 21/553 (2013.01); G01N 21/648 (2013.01); G01N 33/53 (2013.01); G01N 33/54373 (2013.01)

(58) Field of Classification Search
CPC .. G01N 21/6428; G01N 21/648; G01N 33/53; G01N 33/54373; G01N 21/553
See application file for complete search history.

(56) References Cited

U.S. PATENT DOCUMENTS 5,987,346 A * 11/1999 Benaron et al.
2004/0023293 A1 * 2/2004 Kreimer ............... B01J 13/0008
506/6
(Continued)

FOREIGN PATENT DOCUMENTS

JP 11023575 A 1/1999
JP H11242031 A 9/1999
(Continued)

OTHER PUBLICATIONS

Matveeva et al., Red blood cells do not attenuate the SPCE fluorescence in surface assays, Anal Bioanal Chem, 388: pp. 1127-1135, published online May 30, 2007.*
(Continued)

Primary Examiner — Rebecca L Martinez
(74) Attorney, Agent, or Firm — Cantor Colburn LLP

(57) ABSTRACT

At least an embodiment addresses the problem of providing a SPR (surface plasmon resonance) or SPFS (surface plasmon-field enhanced fluorescence spectroscopy) immunoassay, which enables the measurement of whole blood, undergoes little fluctuations in measurement values, and can measure whole blood, serum and plasma in a single apparatus. At least an embodiment solves the above-mentioned problem by a SPR or SPFS immunoassay, which is an immunoassay utilizing SPR or SPFS, including an absorbance measurement step of measuring an absorbance of a sample, a mode setting step of setting a mode that corresponds to the result of the absorbance measured in the absorbance measurement step, and one or multiple step(s) for which treatment condition(s) has/have been set in accordance with the mode set in the mode setting step.

16 Claims, 4 Drawing Sheets

(51) Int. Cl.
*G01N 33/543* (2006.01)
*G01N 33/53* (2006.01)

(56) References Cited

U.S. PATENT DOCUMENTS

2009/0097022 A1* 4/2009 Shen et al.
2011/0188030 A1 8/2011 Verschuren et al.

FOREIGN PATENT DOCUMENTS

| JP | 2001296292 A | 10/2001 |
| JP | 2002107365 A | 4/2002 |
| JP | 2006078364 A | 3/2006 |
| JP | 2012007930 A | 1/2012 |
| WO | 2007007849 A1 | 1/2007 |
| WO | 2009087519 A2 | 7/2009 |

OTHER PUBLICATIONS

Extended European Search Report corresponding to Application No. 13843487.3-1554/2905617 PCT/JP2013/074399; dated Jul. 12, 2016.
International Search Report corresponding to Application No. PCT/JP2013/074399; dated Dec. 10, 2013, with English translation.
Written Opinion of the International Searching Authority corresponding to International application No. PCT/JP2013/074399; dated Dec. 10, 2013, with English translation.
European Office Action for corresponding EP Patent Application No. 13843487.3-1554; dated Sep. 21, 2017.

* cited by examiner

IMMUNOASSAY METHOD UTILIZING SURFACE PLASMON

This is the U.S. national stage of application No. PCT/JP2013/074399, filed on Sep. 10, 2013. Priority under 35 U.S.C. § 119(a) and 35 U.S.C. § 365(b) is claimed from Japanese Application No. 2012-221362, filed Oct. 3, 2012, the disclosure of which is also incorporated herein by reference.

TECHNICAL FIELD

The present invention relates to an immunoassay utilizing surface plasmon that enables the measuring of whole blood.

BACKGROUND ART

A biochemical examination of blood is generally conducted on plasma or serum as a subject. Plasma is prepared by collecting about 10 mL of venous blood by a syringe and centrifuging the venous blood. In an immune examination of an item relating to infectious diseases, serum is used as a measuring sample, but at least about 30 minutes of treatment time, which is the sum of a time for solidifying blood and a time for the subsequent centrifugation, is required for obtaining serum from whole blood.

Therefore, medical staffs require great care and time, and this is sometimes harmful to the life of a patient especially in an emergency case such as a cardiac disease. Furthermore, in an emergency operation in which an immediate judgment to determine whether or not a patient has an infectious disease such as hepatitis or HIV is required, the development of a more rapid measuring method in which an examination time after collection of blood is shorten has been desired.

Examples of immune assays include a radioimmunoassay (RIA), an enzyme immunoassay (EIA), a particle agglutination process, a counting immunoassay and the like, and in RIA and EIA, it is necessary to conduct an antigen-antibody reaction and then conduct B/F separation, and thus great care and time are required until a measuring result is obtained.

As a means that responds to this demand, a measuring method that enables the measurement of whole blood by forcedly conducting hemolysis in a latex particle turbidimetry is exemplified. For example, Patent Literature 1 suggests a whole blood immunoassay that aims at removing the effect of hemocytes without affecting an antigen-antibody reaction in a whole blood immunoassay. This immunoassay is a method including mixing a whole blood sample and immunized insoluble carrier particles to thereby allow an immuneagglutination reaction, diluting the obtained flocculated reaction mixture with an aqueous solution containing an erythrocyte-lysing agent to lyse erythrocytes to thereby prepare a measuring sample, and measuring the agglomeration degree of the measuring sample. Furthermore, Patent Literature 2 suggests an immunoassay aiming at providing data with fine accuracy, by which a measurement can be conducted conveniently within a short time without pretreating blood by a centrifuge or the like, which uses a sample obtained by lysing hemocytes consciously and forcedly by a method that does not affect an immune reaction and combining the sample with various quantification agents. This immunoassay is a method including subjecting an antigen or antibody in a subject sample and insoluble particles on which an antibody or antigen that specifically reacts with the antigen or antibody in the subject sample is fixed, and an antigen or an antibody in a subject sample are subjected to an agglutination reaction, and measuring the change in absorbance or change in scattered light by the irradiation of the obtained flocculate mixed liquid with light, wherein whole blood is used as the subject sample, and the whole blood is forcedly lysed.

CITATION LIST

Patent Literatures

Patent Literature 1: JP 2002-107365 A
Patent Literature 2: JP 2001-296292 A
Patent Literature 3: JP 11-23575 A

SUMMARY OF INVENTION

Technical Problem

The latex particle turbidimetry suggested in the past has a problem of the effect of use of a high concentration of a surfactant on an immune reaction during hemolysis, and a problem that the method has not achieved the level of sensitivity required by the markets in an examination item for which highly sensitive measuring is required.

In the area of immunoassays in which such demand for increasing of the sensitivity has been increasing, SPR (Surface Plasmon Resonance) or SPFS (Surface Plasmon-field enhanced Fluorescence Spectroscopy) utilizing surface plasmon gains attentions as an effective measurement method. For example, Patent Literature 3 suggests about an immunoassay system using SPR or SPFS intended for whole blood. Specifically, the method is a method for measuring a myocardial infarction marker, including administering whole blood to a measurement chip for a surface plasmon resonance biosensor including a transparent substrate, a metal film disposed on the transparent substrate, and an antibody against a myocardial infarction marker, which is fixed on the metal film.

However, Patent Literature 3 does not describe about a specific treatment method of the immunoassay system using SPR or SPFS; therefore, it is impossible to specifically conduct the treatment method based on this document, and thus the method cannot be put into practical use.

The present invention has been made so as to solve the above-mentioned problem, and the object thereof is to provide a SPR or SPFS immunoassay, which enables the measurement of whole blood, undergoes little fluctuations in measurement values, and can measure whole blood, serum and plasma in a single apparatus.

Solution to Problem

The present inventors have considered about an immunoassay utilizing surface plasmon (SPR or SPFS) intended for the measurement of whole blood. During the process of the consideration, they found a SPR or SPFS immunoassay by which whole blood, serum and plasma can be measured in a single apparatus, and which undergoes little fluctuations in measurement values by variously changing treatment conditions, and completed the present invention.

Namely, in an aspect of the present invention, the immunoassay according to the present invention for solving the above-mentioned problem is an immunoassay utilizing SPR (surface plasmon resonance) or SPFS (surface plasmon-field enhanced fluorescence spectroscopy), including an absorbance measurement step of measuring an absorbance of a sample, and a mode setting step of setting a treatment mode that differs in accordance with the result of the absorbance measured in the absorbance measurement step.

Specifically, a sample is classified depending on the absorbance, and the mode for each treatment is set in accordance with the absorbance. For example, whole blood contains hemocyte components, whereas serum or plasma is substantially free from hemocyte components. Therefore, by measuring the absorbance of the wavelength absorbed by the hemocyte components, and the absorbance of the wavelength that is not absorbed by the hemocyte components as a standard, it becomes possible to determine whether a sample is whole blood, or serum or plasma.

In the mode setting step that is subsequently conducted, the sample is classified based on the measurement result obtained in the absorbance measurement step (for example, the sample is classified into whole blood sample, or serum or plasma sample), and a treatment to select a mode in accordance with the classification is conducted. In addition, as mentioned below, in the case when treatment conditions of one or multiple step(s) are set (changed) in accordance with the mode set in the mode setting step, such processing on the system can also be conducted in this mode setting step.

Since measurings corresponding to multiple modes can be conducted in a single apparatus, it becomes possible to conduct an immunoassay by SPR or SPFS irrespective of the kind of the sample.

The number of the mode set in the mode setting step is not especially limited, and may be two modes of "whole blood mode" and "serum/plasma mode" as mentioned below, or may be three or more modes. For example, it is also possible to classify the sample more finely based on the measurement result in the absorbance measurement step and adjust the treatment conditions more precisely so that the treatment conditions become appropriate to the respective classified samples.

Furthermore, in an aspect of the present invention, the immunoassay according to the present invention can include, after the mode setting step, one or multiple step(s) having different treatment condition(s) in accordance with the treatment mode set in the mode setting step.

Namely, in the case when a specific mode is selected in the above-mentioned mode setting step, it becomes possible to conduct one or multiple step (s) under a treatment condition that is different from other mode that is frequently used (normal mode) depending on the selected specific mode, i.e., under a more suitable treatment condition. The each step in the case when a specific mode is not selected, or a step that is a specific mode but may be conducted under a similar treatment condition to that of the normal mode, can be conducted under the original treatment condition that has been set in advance.

Furthermore, in an aspect of the present invention, the immunoassay according to the present invention is preferably such that a measuring mode using whole blood as a sample (whole blood mode) and a measuring mode using serum or plasma as a sample are set in the above-mentioned mode setting step.

By switching the whole blood mode and the serum/plasma mode in the mode setting step, and adjusting the subsequent measuring system to an exemplary embodiment that is suitable for the above-mentioned each mode, whole blood, serum and plasma can be measured in a single apparatus, and thus it becomes unnecessary to use different apparatuses according to the sample.

The difference in absorbance reflects the difference in content of the hemocyte components, and the amount of adhesion of the hemocyte component or foreign substances to the sensor substrate, or the efficiency of the contact of a substance to be measured with the sensor substrate differ depending on the difference in content of the hemocyte components. Therefore, it is suitable to adjust the treatment conditions of the following steps depending on the difference in absorbance so that the measuring by SPR or SPFS is suitably conducted.

Some examples in which, for example, in the case when the whole blood mode is selected in the above-mentioned mode setting step, it is preferable to conduct measurement with changing the treatment condition of a general serum/plasma mode in the subsequent measuring system (in other words, to conduct measurement under a different treatment condition that has been changed in accordance with the set mode), will be exemplified below.

A preferable example as the above-mentioned treatment condition that differs in accordance with the set mode is, in the case when a labeling reaction step is conducted after the primary reaction step, a number of times of washing in a washing step that is conducted before the labeling reaction step (first exemplary embodiment).

According to this, with respect to the washing of the sensor substrate conducted after the primary reaction step and before the labeling reaction step, the adhesion of the hemocyte components in the whole blood or the foreign substances in blood to the sensor substrate can be suppressed in the whole blood mode while suppressing addition of excess washing to the serum/plasma mode, by selecting a suitable number of times of washing in accordance with the sample.

Furthermore, a preferable another example of the treatment condition that differs in accordance with the above-mentioned set mode is a dilution rate of the sample in a dilution step (second exemplary embodiment).

According to this, the content of the hemocytes and the content of the foreign substances in the reaction liquid are decreased in, for example, the whole blood mode, by adjusting the dilution rate of a measuring sample depending on the sample, and thus the adhesion of the hemocyte components in the whole blood or the foreign substances in blood to the sensor substrate can be suppressed even by an equivalent washing condition to that of the serum/plasma mode (normal mode). Furthermore, since whole blood contains a large content of hemocyte components, the apparent viscosity of the sample becomes high and the diffusion factor becomes small, and as a result thereof, the reaction rate of the substance to be measured in whole blood is considered to become lower than the reaction rate of the substance to be measured in serum or plasma. Therefore, in the case of the whole blood mode, it is preferable to increase the dilution rate so as to be higher than that in the serum/plasma mode, so that the reaction rate (antigen capture rate) between the substance to be measured and a solid phase ligand is equalized in any sample.

Furthermore, another preferable example of the above-mentioned treatment condition that differs in accordance with the set mode is a time for a primary reaction step (sometimes also referred to as "primary reaction time") (third exemplary embodiment).

Even in the case when a substance to be measured in the same amount is contained, a different measurement result may be obtained depending on the characteristic of the sample. For example, Furthermore, it is considered that, since whole blood contains a large content of hemocyte components, the apparent viscosity of the sample becomes high and the diffusion factor becomes small, and as a result thereof, the reaction rate of the substance to be measured in whole blood becomes lower than the reaction rate of the substance to be measured in serum or plasma. Therefore, in the case of the whole blood mode, it is preferable to extend the primary reaction time so as to be longer than that for the serum/plasma mode, so that the reaction rate (antigen capture rate) between the substance to be measured and a solid phase ligand is equalized in either sample. The primary reaction step herein refers to a step of bringing a sample containing a substance to be measured (for example, an antigen) into contact with the surface of a sensor substrate having a solid phase ligand (for example, an antibody), as in a general immunoassay in SPR or SPFS.

In an aspect of the present invention, it is preferable to set a mode for a whole blood sample and a mode for a serum sample or a plasma sample in the above-mentioned mode setting step in the immunoassay according to the present invention.

Furthermore, it is preferable that the above-mentioned mode setting step is a step of setting a whole blood mode for a whole blood sample and a normal mode for a serum sample or a plasma sample, and the number of times of washing in the whole blood mode is more than that for the normal mode.

Furthermore, it is preferable that the above-mentioned mode setting step is a step of setting a whole blood mode for a whole blood sample and a normal mode for a serum sample or a plasma sample, and the dilution rate in the whole blood mode is higher than that for the normal mode.

Moreover, it is preferable that the above-mentioned mode setting step is a step of setting a whole blood mode for a whole blood sample and a normal mode for a serum sample or a plasma sample, and the time for the primary reaction step in the whole blood mode is longer than that for the normal mode.

In an aspect of the present invention, it is preferable that the immunoassay according to the present invention is an immunoassay utilizing surface plasmon-field enhanced fluorescence spectroscopy.

The immunoassay system according to the present invention for solving the above-mentioned problem utilizes the SPR or SPFS immunoassay described above. Specifically, the system can be constructed by connecting a means for conducting the SPR or SPFS immunoassay according to the present invention (an apparatus, a program or the like) in a cooperative manner.

Advantageous Effects of Invention

According to the immunoassay utilizing surface plasmon and the system utilizing the immunoassay according to the present invention, an immunoassay apparatus used for serum or plasma can be utilized in the measurement of whole blood, and thus it is possible to respond to the needs of rapid diagnosis of POCT. For example, when whole blood is applied as a sample to a measuring apparatus that is presupposed to be used by using serum or plasma as a sample, problems such as fluctuations in measurement values and the like occur, whereas, according to the present invention, when a mode for whole blood is set in the mode setting step, various treatment conditions that are suitable for the measurement in the case when whole blood is used as a sample are set in the subsequent step for setting treatment conditions, and a measurement is conducted after that treatment, the fluctuations in measurement values can be decreased, and thus an extremely accurate measurement result can be obtained. On the other hand, since a mode for serum or plasma is set in the mode setting step also in the case when serum or plasma is used as a sample, similar rapidness of treatment to that in conventional methods can be maintained in a single apparatus, and only small amounts of agents are required.

DESCRIPTION OF EMBODIMENTS

The immunoassay according to the present invention will be explained in detail with exemplifying the case when a measurement based on SPFS is conducted by using samples derived from blood such as whole blood, serum and plasma as specific samples. The present invention is not limited to the following embodiments, and can be variously modified and conducted within the scope of the gist thereof.

Firstly, it is necessary to classify a sample by an absorbance and set a mode so as to apply a preferable treatment condition, and the treatment condition can be set so as to be able to be applied to various exemplary embodiments. Furthermore, it is also possible to set the treatment condition so as to apply to the case when a measurement is conducted by SPR instead of SPFS.

In an aspect of the present invention, the immunoassay according to the present invention include an absorbance measurement step of measuring an absorbance of a sample, a mode setting step of setting a mode that corresponds to the result of the absorbance measured in the absorbance measurement step, and a treatment condition setting step of setting a condition for treating the sample. The cases when each treatment condition in the treatment condition setting step is changed will be explained below.

<Immunoassay of Sample>

Figure 1:
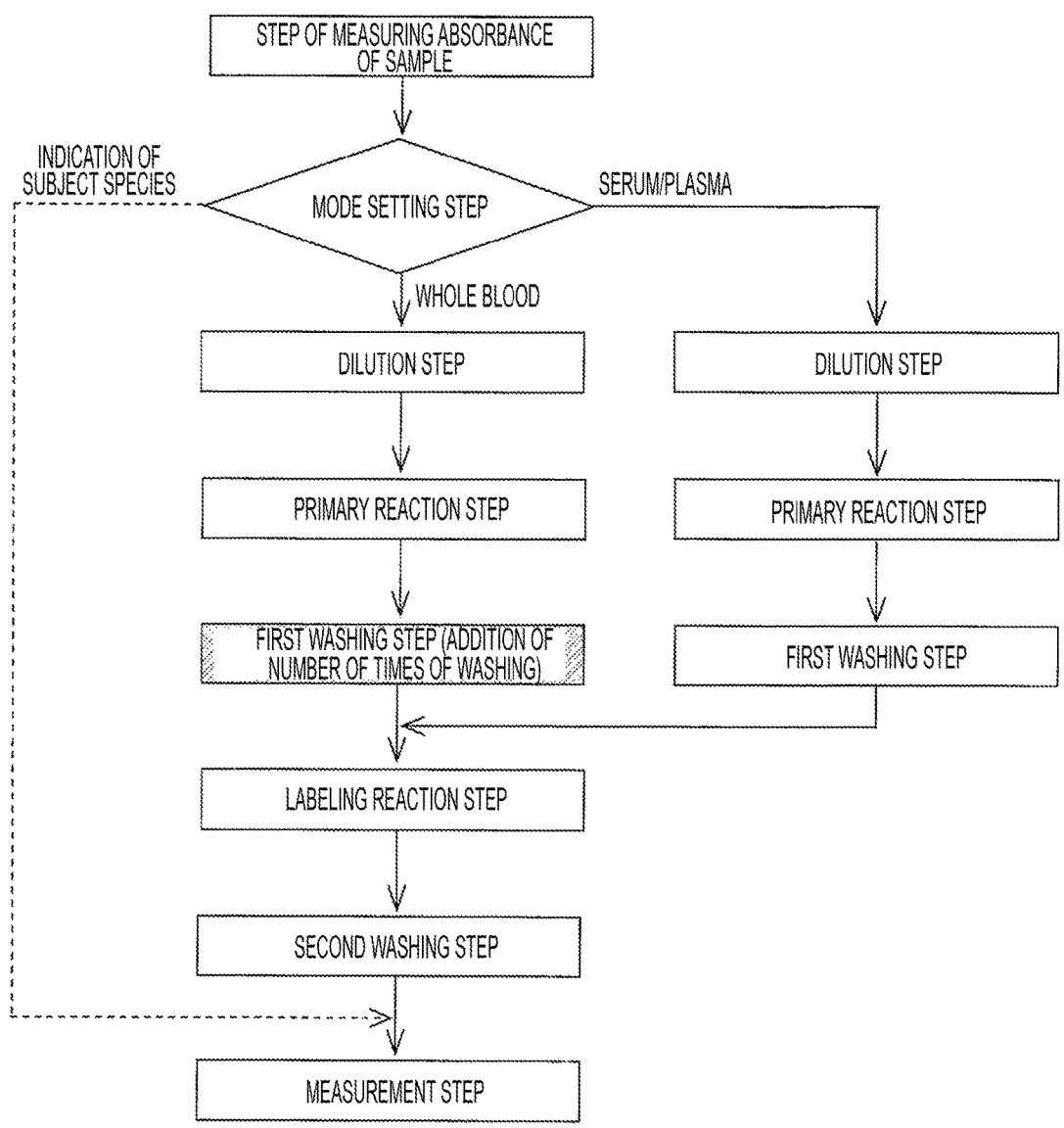
FIG. 1 is an evaluation flow chart in which the treatment condition that differs in accordance with the set mode is a number of times of washing.

First Exemplary Embodiment: In the Case when the Treatment Condition that Differs in Accordance with the Set Mode is a Number of Times of Washing As shown in FIG. 1, in the immunoassay utilizing surface plasmon according to this embodiment, a step of measuring an absorbance of a sample and a mode setting step of setting a treatment mode (a step of setting a whole blood mode and a serum/plasma mode) are firstly conducted. In this mode setting step, the treatment mode is isolated. In the case when the treatment mode is set to "whole blood mode" in accordance with the result of the measurement of the absorbance, a dilution step of diluting the sample at a general dilution rate, a primary reaction step, a first washing step to which a number of times of washing has been added more than that in a general first washing step, a labeling reaction step, a second washing step, and a measurement step are sequentially conducted. In conducting on a SPR immunoassay, the flow may be generally considered to be a flow in which the labeling reaction step and second washing step are omitted in the above-mentioned flow.

On the other hand, the case when the treatment mode is set to "serum/plasma mode" will be mentioned below.

(Absorbance Measurement Step)

The absorbance measurement step is a step for measuring the absorbance of the sample. The method for measuring the absorbance is not especially limited, and known various means can be used, and for example, the measurement can be conducted by using similar units to those of a general spectrometer (a container for housing a sample, a white light source lamp, a prism, a slit, a light detector and the like). The absorbance measurement step is generally conducted before the various treatments in which the conditions are likely to be changed depending on the sample (for example, a dilution treatment), but it is not necessary that the measurement step is conducted immediately before the sample dilution step, and the measurement step may be conducted after treatments that are common in the respective samples are conducted.

(Mode Setting Step)

The mode setting step is a step of automatically discriminating the sample by selecting a whole blood mode intended for whole blood and a serum and plasma mode intended for serum or plasma. The whole blood refers to blood collected from a human or other animal, which has not undergone a treatment for separating serum and plasma. The plasma refers to blood from which hemocyte components have been removed, and the serum refers to plasma from which fibrinogen and coagulation factors have been removed (by coagulation).

In this mode setting step, the specific exemplary embodiment thereof is not especially limited as long as the mode can be suitably switched by utilizing the result of the measurement of the absorbance. For example, in the case when a whole blood mode and a serum/plasma mode are to be set, exemplified is an exemplary embodiment in which an absorbance of a wavelength absorbed by the erythrocyte component (for example, 540 nm) is obtained, and a whole blood mode is set with determining that the sample is whole blood in the case when the absorbance is at a certain threshold value or more, or, conversely, a serum/plasma mode (normal mode) is set with determining that the sample is serum or plasma in the case when the absorbance is at less than a certain threshold value sample.

Furthermore, further preferably, it is also possible to determine and set a whole blood mode or a serum/plasma mode (normal mode) by obtaining the difference or ratio of an absorbance of a wavelength that is absorbed by an erythrocyte component (for example, 540 nm) and an absorbance of a wavelength that is not absorbed by hemocyte components (for example, 700 nm). In the latter case, since the color tone of plasma is canceled, the measuring is difficult to be affected by each sample (each subject) and thus the measuring can be conducted at a high accuracy.

(Dilution Step)

The dilution step is a step of diluting a sample so that the respective steps relating to the measuring of SPFS can be suitably conducted. The dilution rate of the sample is not especially limited, and can be suitably set depending on the exemplary embodiment of the measuring system, the amount of the collected sample, the flow amount in the liquid sending to the sensor substrate, the viscosity of the sample (the amount of the hemocyte components in whole blood) and the like, and is generally from 2 to 10 times, preferably from 2 to 6 times. The dilution method is also not especially limited, and a suitable amount of solvent (PBS (phosphate buffer saline), TBS (tris buffer saline) and the like) may be added to the sample according to a conventional method.

(Primary Reaction Step)

The primary reaction step is a step of bringing the sample into contact with a sensor substrate. By this step, a complex of an analyte (antigen), which is the substance to be measured in the sample, and a ligand (antibody) immobilized on the surface of the sensor substrate is formed.

The time for the primary reaction step, i.e., the time for bringing the sample into contact with the sensor substrate is adjusted depending on the amount of the substance to be measured included in the sample, and the like, in some cases, and is generally from 3 to 30 minutes, preferably generally from 5 to 20 minutes.

(First Washing Step)

The first washing step is a step of washing the sensor substrate by feeding a washing liquid by liquid sending or the like after the primary reaction step and before the labeling reaction step. By conducting the first washing step, foreign substances in blood (proteins, sugar lipids and the like other than the substance to be measured) and hemocyte components that have been non-specifically adsorbed on the surface of the sensor substrate in the primary reaction step can be removed. By this way, the further non-specific binding of the labeling antibody used in the labeling reaction step to the above-mentioned non-specifically adsorbed substances and the appearance of the labeled antibody as a noise in the measurement step can be suppressed.

As the washing liquid, a solution formed by adding a suitable amount of surfactant (for example, Polyoxyethylene (20) Sorbitan Monostearate (trade name: Tween 20), Tween 80, TritonX-100, Digitonin) to a solvent such as PBS (phosphate buffer saline), TBS (tris buffer saline) or the like, or the like can be used. The amount of the surfactant to be added can be suitably adjusted depending on the kind of the surfactant used, and for example, when the surfactant is "Tween 20", the amount is generally from 0.01 wt % to 0.5 wt %.

Furthermore, in a system that is constituted by including a sensor substrate and a flow path formed on the surface thereof so that the sample, washing liquid and the like are subjected to reciprocating liquid sending in that flow path, the conditions such as the liquid amount, time and the like in the reciprocating liquid sending of the washing liquid in the flow path can be suitably set by using the conditions in the case when plasma/serum is used as a sample (normal mode) as standards, and by considering an exemplary embodiment of a SPFS measurement system (the sizes of the sensor substrate and flow cell, and the like). The liquid amount of the washing liquid is generally from 50 to 500 μL, preferably from 100 to 200 μL, more preferably 150 μL. Furthermore, the time for conducting the reciprocating liquid sending of the washing liquid per one washing treatment is generally from 0.5 to 20 minutes, preferably from 3 to 10 minutes.

The first washing step may include one or multiple washing treatment (s). Meanwhile, the time during bringing the washing liquid into contact with the sensor substrate, in other words, the time during subjecting the washing liquid to the reciprocating liquid sending in a system conducting reciprocating liquid sending, i.e., the time from the liquid sending of the washing liquid to the sensor substrate to the completion of the reciprocating liquid sending and ejection of the washing liquid is counted as one washing treatment. A time for liquid sending of a solvent other than the washing liquid (a solvent that does not affect the reaction) can be interposed between the two washing treatments, or the washing treatments may be continuously conducted without interposing such time.

In the first exemplary embodiment, in the case when a whole blood mode is selected, the number of times of the washing treatment is added. According to the finding obtained by the present inventors, the effect of washing is more excellent in the case when multiple washing treatments are conducted with replacing the washing liquid, than in the case when the washing liquid is subjected to reciprocating liquid sending for a long time per one washing treatment.

The number of times of the washing treatment(s) included in the first washing step can be suitably adjusted with considering the effect of the washing, and the serum/plasma mode (normal mode) includes generally 2 to 6 times, preferably 3 to 4 times, more preferably 3 times of washing treatments.

In response to this, in the first exemplary embodiment of the whole blood mode, the number of times of washing is such that 1 to 3 time(s), more preferably 2 times of additional washings is/are further conducted in addition to the serum/plasma mode (normal mode).

(Labeling Reaction Step)

The labeling reaction step is a step of bringing a labeled antibody labeled with a fluorescent substance into contact with the sensor substrate. In the case when an antigen has bound to the immobilized antibody on the surface of the sensor substrate to thereby form a complex in the primary reaction step, the labeled antibody further binds to the captured antigen to form a complex formed of the immobilized antibody—the antigen—the labeled antibody. This step can be conducted in accordance with a general SPFS measurement system.

(Second Washing Step)

The second washing step is a step of conducting liquid sending of a washing liquid after the labeling reaction step and before the measurement step. By conducting the second washing step, the labeled antibody that has been nonspecifically adsorbed on the surface of the sensor substrate in the labeling reaction step can be removed, thereby the appearance of the labeled antibody as a noise in the measuring can be suppressed.

The kind and concentration of the surfactant, the liquid amount, the time and the like in feeding the washing liquid by reciprocating liquid sending or the like in the second washing step can be similar to those in the first washing step, or different conditions may be set as necessary.

(Measurement Step)

In the SPFS measurement system, the measurement step is a step in which light having a specific excitation wavelength is irradiated from the rear surface of the sensor substrate, and the intensity of the light having a specific fluorescence wavelength generated by the irradiation is measured by a light amount detection sensor such as a PMT (photomultiplier tube) disposed on the upper surface of the sensor substrate. If the predetermined substance to be measured (antigen) is present in the sample and an immobilized antibody-antigen-labeled antibody has been formed in the labeling reaction step, the fluorescence emitted by the fluorescent substance in the complex by being excited by an enhanced evanescent wave by SPFS can be measured by a PMT or the like. This step can be conducted according to a general SPFS measurement system. The result of the measurement of the fluorescence amount is output and analyzed by a suitable information processing means, and a quantitative or qualitative analysis of the substance to be measured in the sample can be conducted based on the measurement result.

In the case when whole blood is used as a sample, a certain volume in the whole blood sample is occupied by hemocyte components, and thus the volume in which the substance to be measured (antigen) is included is a part of the sample (roughly estimated by total volume×(100−hematocrit value (%))). Furthermore, as shown in the exemplary embodiment mentioned below, in the case when whole blood is used as a sample, a dilution rate that is different from that in the case when serum or plasma is used as a sample is sometimes used. With consideration for such difference, it is necessary to calculate the concentration of the substance to be measured after conducting suitable arithmetic processings for the case when whole blood is used as a sample and the case when serum or plasma is used as a sample, respectively.

On the other hand, in the case when the treatment mode is set to "serum/plasma mode" in the mode setting step (isolation of the treatment mode), as shown in FIG. 1, a dilution step of diluting a sample at a general dilution rate, a primary reaction step, a first washing step in which the number of times of washing is a general number, a labeling reaction step, a washing step and a measurement step are sequentially conducted.

Since the explanations on the respective steps are similar to those in the above-mentioned "whole blood mode", the explanations are omitted here.

Figure 2:
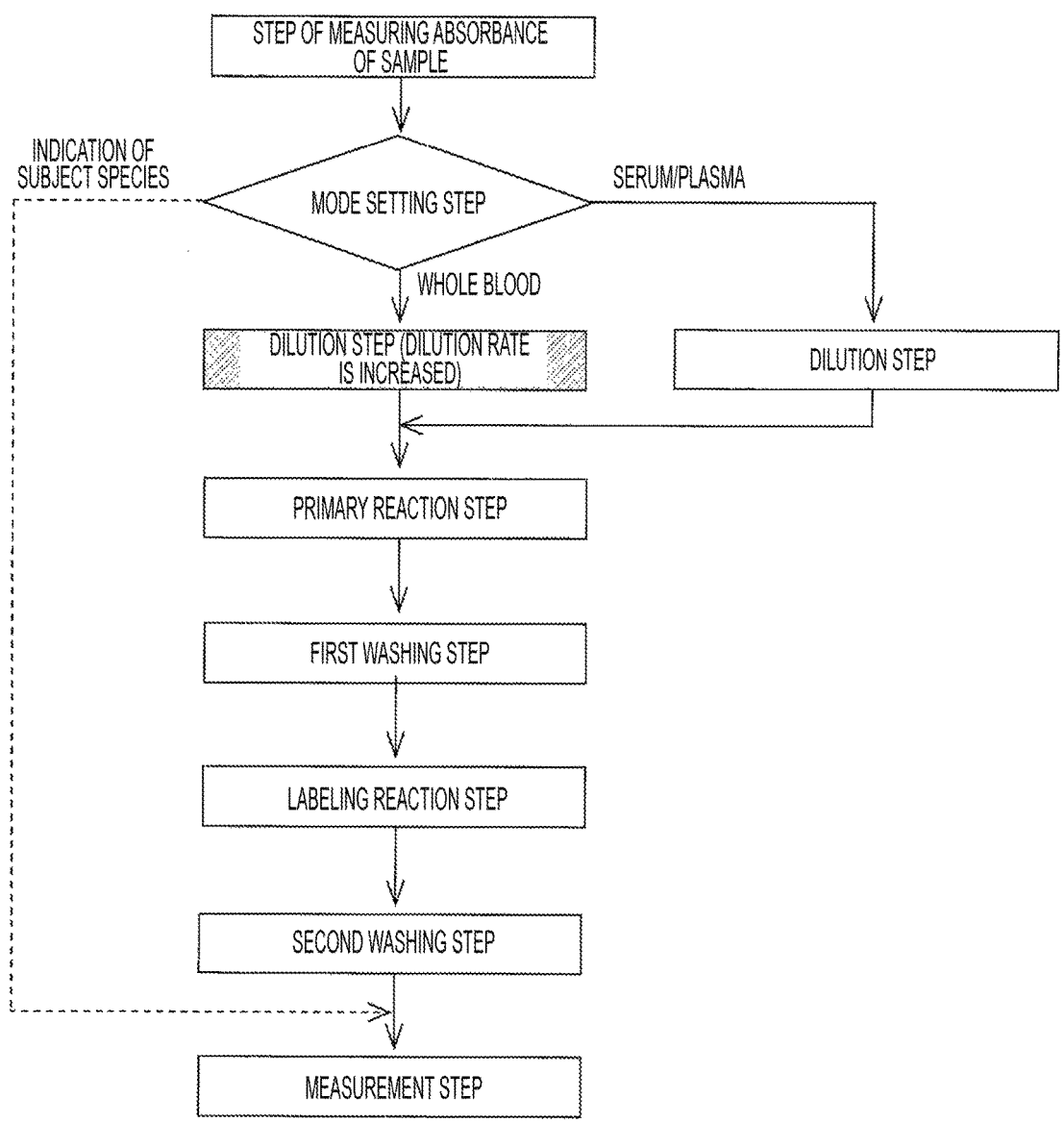
FIG. 2 is an evaluation flow chart in which the treatment condition that differs in accordance with the set mode is a dilution rate.

Second Exemplary Embodiment: The Case when the Treatment Condition that Differs in Accordance with the Set Mode is a Dilution Rate In the immunoassay utilizing surface plasmon according to this embodiment, as shown in FIG. 2, a step of measuring an absorbance of a sample, and a mode setting step of setting a treatment mode (a whole blood mode or a serum/plasma mode) are firstly conducted. In this mode setting step, the treatment mode is isolated.

In the case when the treatment mode is set to "whole blood mode" in accordance with the result of the measurement of the absorbance, a dilution step of diluting the sample by increasing the dilution rate is conducted. The dilution rate in "whole blood mode" is from 1.5 to 5 times, more preferably from 2 to 3 times with respect to the serum/plasma mode (normal mode). By diluting the sample with increasing the dilution rate more in the whole blood mode than that in the normal mode, the nonspecific adsorption of the hemocyte components and foreign substances in blood to the sensor substrate is suppressed, whereby the reaction efficiency (antigen capture rate) between the solid phase ligand (antibody) and an analyte, which is the substance to be measured (antigen), can be retained. In other words, to improve the dilution rate in the second exemplary embodiment serves as a substitute for the increasing in the number of times of the washing treatments in the first exemplary embodiment or the extension of the primary reaction time in the third exemplary embodiment, and an effect that rapidness can be retained can be obtained.

Thereafter, a primary reaction step, a first washing step, a labeling reaction step, a second washing step and a measurement step are sequentially conducted. Since the respective steps are similar to those in the first exemplary embodiment, the explanations thereon are omitted here.

On the other hand, in the case when the treatment mode in the mode setting step (isolation of the treatment mode) is set to "serum/plasma mode" in accordance with the result of the measurement of the absorbance, as shown in FIG. 2, a dilution step of diluting a sample at a general dilution rate, a primary reaction step, a first washing step, a labeling reaction step, a second washing step and a measurement step are sequentially conducted. Since the respective steps are similar to those in the first exemplary embodiment, the explanations thereon are omitted here.

Figure 3:
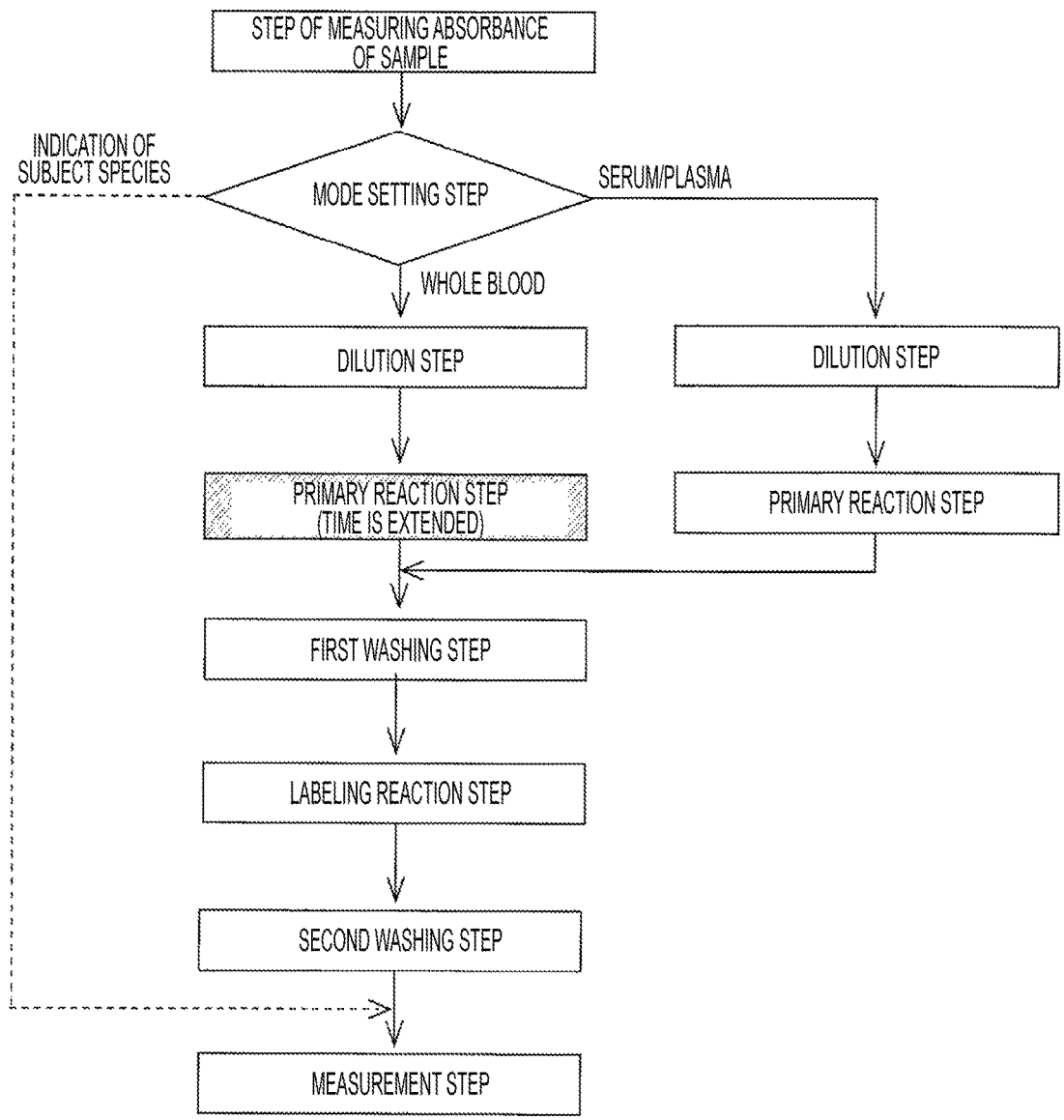
FIG. 3 is an evaluation flow chart in which the treatment condition that differs in accordance with the set mode is a primary reaction time.

Third Exemplary Embodiment: In the Case when the Treatment Condition that Differs in Accordance with the Set Mode is a Primary Reaction Time In the immunoassay utilizing surface plasmon according to this embodiment, as shown in FIG. 3, a step of measuring an absorbance of a sample, and a mode setting step of setting a treatment mode (a whole blood mode or a serum/plasma mode) are firstly conducted. In this mode setting step, the treatment mode is isolated.

In the case when the treatment mode is set to "whole blood mode" in accordance with the result of the measurement of the absorbance, a dilution step of diluting a sample at a general dilution rate, and a primary reaction step in which a primary reaction time is extended are conducted. The extended time for the primary reaction step in the third exemplary embodiment is from 1.2 times to 4 times, more preferably from 1.5 times to 2 times as long as that in the serum/plasma mode (normal mode). By extending the time for the primary reaction step more than that in the normal mode, an effect that the reaction efficiency (antigen capture rate) between the solid phase ligand (antibody) and an analyte, which is the substance to be measured (antigen) can be retained also in the whole blood mode can be obtained. Thereafter, a first washing step, a labeling reaction step, a second washing step and a measurement step are sequentially conducted. Since the respective steps are similar to those in the first exemplary embodiment, the explanations thereon are omitted here.

On the other hand, in the case when the treatment mode in the mode setting step (isolation of the treatment mode) is set to "serum/plasma mode" in accordance with the result of the measurement of the absorbance, as shown in FIG. 3, a dilution step of diluting a sample at a general dilution rate, a primary reaction step, a first washing step, a labeling reaction step, a second washing step and a measurement step are sequentially conducted. Since the respective steps are similar to those in the first exemplary embodiment, the explanations thereon are omitted here.

Figure 4:
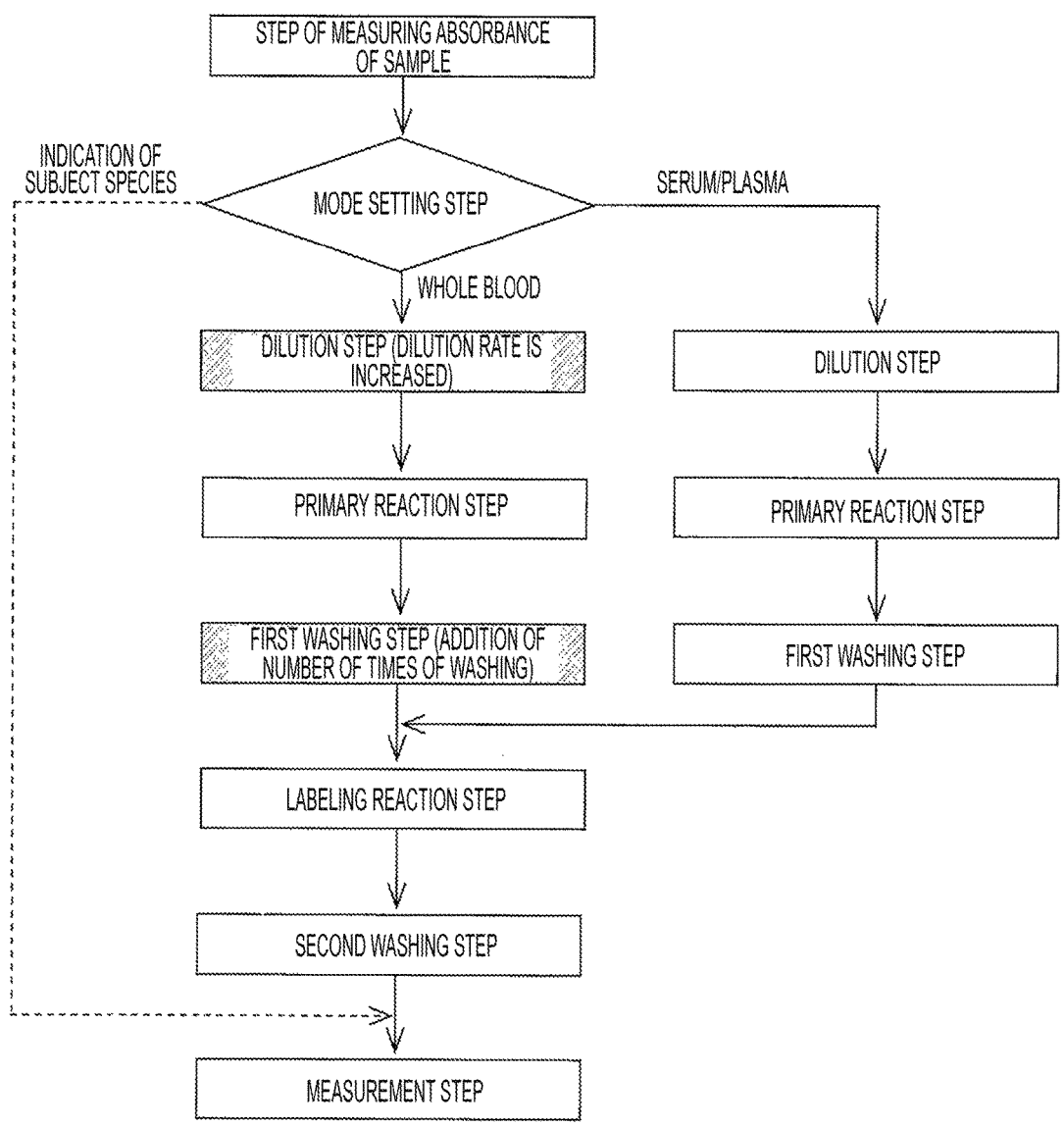
FIG. 4 is an evaluation flow chart in which the treatment conditions that differ in accordance with the set mode are a number of times of washing and a dilution rate. In each drawing, the step indicated by a shaded area of diagonal lines indicates a step under a treatment condition that differs from that in the serum/plasma mode (normal mode), in the case when a whole blood mode is selected.

Fourth Exemplary Embodiment: In the Case when the Treatment Conditions that Differ in Accordance with the Set Mode are a Number of Times of Washing and a Dilution Rate In the immunoassay utilizing surface plasmon according to this embodiment, as shown in FIG. 4, a step of measuring an absorbance of a sample, and a mode setting step of setting a treatment mode (a whole blood mode or a serum/plasma mode) are firstly conducted. In this mode setting step, the treatment mode is isolated.

Here, in the case when the treatment mode is set to "whole blood mode" in accordance with the result of the measurement of the absorbance, a dilution step for diluting a sample with increasing a dilution rate, a primary reaction step, a first washing step in which number of times of washing has been added more than that in a general first washing step, a labeling reaction step, a second washing step, and a measurement step are sequentially conducted. The conditions for the dilution step for diluting a sample with increasing a dilution rate and for the first washing step in which a number of times of washing has been added can be similar to those for the first exemplary embodiment and second exemplary embodiment; however, with consideration for that the effect is enhanced by combining the two special steps, it is possible to mitigate the conditions for the respective steps more than those of the first exemplary embodiment and second exemplary embodiment (to make the conditions closer to those of the normal mode, for example, to decrease the increase rate of the dilution rate and decrease the number of times of the added washing steps) to the extent that the effect that is comprehensively obtained in the fourth exemplary embodiment becomes a sufficient effect that is equivalent to the effect obtained in the first exemplary embodiment and second exemplary embodiment. Since the respective steps, except for the step in which a different treatment is conducted between "whole blood mode" and "serum/plasma mode", are similar to those in the first exemplary embodiment, the explanations thereon are omitted here.

On the other hand, in the case when the treatment mode in the mode setting step (isolation of the treatment mode) is set to "serum/plasma mode" in accordance with the result of the measurement of the absorbance, as shown in FIG. 4, a dilution step of diluting a sample at a general dilution rate, a primary reaction step, a first washing step, a labeling reaction step, a second washing step and a measurement step are sequentially conducted. Since the respective steps are similar to those in the first exemplary embodiment, the explanations thereon are omitted here.

Other Exemplary Embodiments

By either of exemplary embodiments such as embodiments in which the different treatment conditions are combination of "change (addition) of the number of times of washing" and "change (extension) of the primary reaction time", combination of "change (increase) of dilution rate" and "change (extension) of the primary reaction time", combination of "change (addition) of the number of times of washing", "change (increase) of the dilution rate" and "change (extension) of the primary reaction time", and the like, an immunoassay of a sample can be conducted.

<Surface Plasmon Sensor (Sensor Substrate)>

The surface plasmon sensor refers to a structure for measuring signals by SPFS or the like, which is constituted by at least a dielectric element (a prism or a transparent plane substrate), a metal thin film formed on the upper layer of the dielectric element, and a layer including an immobilized ligand formed on the upper layer of the metal thin film (reaction layer).

The metal thin film and the like may be directly formed on the horizontal plane of the prism, but considering the convenience for analyzing many samples and the like, it is desirable that they are formed on the horizontal plane of the prism and on one surface of the removable transparent plane substrate. Furthermore, the reaction layer may be directly formed on the surface of the metal thin film, but where necessary, a spacer layer and/or SAM formed of a dielectric may be formed on the metal thin film, and the reaction layer may be formed thereon.

The surface plasmon sensor can be used in combination with elements that form "flow path" (sheets for forming the side walls of the flow path, top panels and the like) for storing various fluids used for the measurement such as SPFS (a sample liquid, a label ligand solution, a measuring liquid and the like) and for enabling liquid sending by allowing communication among the respective areas. These may be integrated to give an embodiment of a chip-like structure (also referred to as "sensor chip"). Furthermore, an opening for introducing or ejecting a fluid is formed on the surface plasmon sensor, and the opening can be used so as to allow the coming and going between the outside and fluid, by using a pump, or for example, a tube having an approximately oval cross-sectional surface that is formed by a soft element (silicone rubber or the like), or the like.

The conditions at this time (the flow, time and temperature, and the concentrations of the subject and label ligand) can be suitably adjusted.

The surface plasmon sensor or sensor chip can be prepared as follows: in small-lot production (laboratory level), for example, a sensor substrate on which a metal thin film and the like are formed is made in advance, and a sheet or O-ring made of a silicone rubber having a hole having optional shape and size on the center part and a predetermined thickness (the height of a flow path) is put on the surface of the sensor substrate on which the metal thin film and the like have been formed, whereby a side surface structure of a flow path is formed. A light transmittable top panel on which a liquid sending introduction port and a liquid sending ejection port have been formed is then put on the flow path to form a ceiling surface of the flow path, and these are subjected to compression bonding and fixed by attachments such as screws, whereby the surface plasmon sensor or sensor chip can be prepared. Furthermore, in large-lot industrial production (factory level), the sensor chip can be prepared by, for example, forming a metal thin film, a reaction layer and the like on a predetermined region of a transparent plane substrate to give a sensor substrate, while forming a top panel and a side wall element by forming fine concaves and convexes by mold processing of a plastic, photolithography or the like, and combining these.

(Dielectric Element)

As the dielectric element used for the sensor chip, dielectric elements made of glass, and plastics such as polycarbonate (PC), cycloolefin polymer (COP) and the like, preferably dielectric elements made of a material having a refractive index [$n_d$] in the range of from 1.40 to 2.20 at d ray (588 nm), can be used. The thickness in the case when a transparent plane substrate is used as the dielectric element can be adjusted in the range of, for example, from 0.01 to 10 mm. Furthermore, it is preferable that the surface of the dielectric element has undergone a washing treatment with an acid or plasma before the formation of the metal thin film.

(Metal Thin Film)

The metal thin film of the surface plasmon sensor is preferably formed of at least one kind of metal (the metal may be in the form of an alloy) selected from the group consisting of gold, silver, aluminum, copper and platinum, which are stable against oxidation and have a high effect of enhancing electrical field by surface plasmon, and is especially preferably formed of gold. In the case when a plane substrate made of glass is used as the transparent plane substrate, it is preferable to form a thin film of chromium, nickel-chromium alloy or titanium so as to bond the glass and the above-mentioned metal thin film more tightly.

Examples of the method for forming the metal thin film include a sputtering process, deposition processes (resistance heating deposition process, an electron beam deposition process the like), electrolytic plating, a non-electrolytic plating process and the like. It is preferable to form the thin film of chromium and the metal thin film by a sputtering process or a deposition process since the conditions for the formation of the thin film are easily adjusted.

In order to allow easy generation of surface plasmon, the thicknesses of the metal thin films formed of gold, silver, aluminum, copper, platinum, or alloys thereof are each preferably from 5 to 500 nm, and the thickness of the chromium thin film is preferably from 1 to 20 nm. In view of an effect of enhancing an electrical field, it is more preferable that the thicknesses are such that gold: from 20 to 70 nm, silver: from 20 to 70 nm, aluminum: from 10 to 50 nm, copper: from 20 to 70 nm, platinum: from 20 to 70 nm and alloys thereof: from 10 to 70 nm, and the thickness of the chromium thin film is more preferably from 1 to 3 nm.

(Spacer Layer)

For the surface plasmon sensor, where necessary, a spacer layer formed of a dielectric may be formed between the metal thin film and the reaction layer (or SAM) so as to prevent metal quenching of fluorescent pigments by the metal thin film.

As the dielectric, optically transparent various inorganic substances, and natural or synthetic polymers can be used. Among these, it is preferable to use silicon dioxide ($SiO_2$) or titanium dioxide ($TiO_2$) since these are excellent in chemical stability, production stability and optical transparency.

The thickness of the spacer layer is generally from 10 nm to 1 mm, and is preferably 30 nm or less, more preferably from 10 to 20 nm in view of resonance angle stability. On the other hand, the thickness is preferably from 200 nm to 1 mm in view of an effect of enhancing an electrical field, and more preferably from 400 nm to 1,600 nm in view of the stability of the effect of enhancing an electrical field.

Examples of the method for forming the spacer layer made of a dielectric include a sputtering process, an electron beam deposition process, a thermal deposition process, a formation method by a chemical reaction using a material such as a polysilazane, or application by a spin coater, and the like.

(SAM)

For the surface plasmon sensor, where necessary, a SAM (Self-Assembled Monolayer) may be formed between the metal thin film (or a spacer layer) and the reaction layer.

As the molecule for constituting the SAM, a compound having a functional group that can be reacted with the metal thin film and the like (a silanol group, a thiol group or the like) on one terminal of the molecule and having a reactive functional group that can bind to the molecule that constitutes the reaction layer (an amino group, a carboxyl group, glycidyl group or the like) on the other terminal is used. Such compound can be easily obtained as a silane coupling agent or a SAM forming agent. For example, carboxyalkanethiols having a carbon atom number of about 4 to 20 (10-carboxy-1-decanethiol and the like) are preferable since they can form a SAM having low optical effects, i.e., high transparency, low refractive index and thin film thickness. The SAM can be formed by bringing a solution of a molecule that constitutes the SAM (an ethanol solution or the like) into contact with the metal thin film and the like, and binding one functional group of this molecule to the metal thin film and the like.

<Measuring Apparatus>

The surface plasmon sensor (especially one having a form of a sensor chip) can be used by attaching to a known measuring apparatus such as a SPFS or the like. This measuring apparatus essentially includes a light source, a prism, a light detector and the like, and generally further includes a light collecting lens, a cut filter and the like. A means for liquid sending various fluids to a predetermined region at predetermined flow, timing and the like (a liquid sending pump or the like), a computer for controlling various operations and information processings, and the like may be integrated with the above-mentioned measuring apparatus.

Furthermore, the surface plasmon sensor may have an information processing means that memorizes a signal measured by a light detector, and finally calculates and determines the concentration of a substance to be measured in each sample based on a calibration curve and memorizes the information thereof. Furthermore, it is preferable that the surface plasmon sensor has a cut filter for removing noise lights having wavelength components that differ from the fluorescence to be detected, for example, such wavelength components in plasmon scattered light, outer light (illumination light out of an apparatus), excited light (transmitted component of excited light), stray light (scattered component of excited light at each place), autofluorescence emitted by various elements, and the like.

<Measuring Method>

(Sample)

The sample is a substance that is subjected to SPFS or the like, and typical samples include samples derived from blood subjects collected from human, mammals other than human (model animals, pet animals the like) and other animals (whole blood, serum, plasma and the like). During the analysis, where necessary, the sample may be mixed with pure water, saline, buffer, various solvents such as agent solutions and used, or blood subjects may be mixed with an anticoagulant (heparin or the like) or the like and used. Either of such mixed liquid or sample itself, or a solution containing a substance to be measured, which is prepared for a certain purpose, and a fluid that is sent to a predetermined region of the surface plasmon sensor for measuring a signal by SPFS or the like (this includes a solution, a suspension liquid, a sol, and other substance having fluidity) is encompassed in the sample.

(Substance to be Measured)

A substance to be quantified or detected by SPFS or the like refers to "substance to be measured". Any substance that can be captured by the surface of the sensor can be a substance to be measured without special limitation, and typical substances to be measured includes proteins (including polypeptides, oligopeptides and the like) or complexes thereof that serve as tumor markers. Furthermore, cells, viruses and the like having sites that are recognized by ligands (epitopes and the like) on the surface may also be substances to be measured.

Furthermore, without limiting to an immunoassay using an antigen antibody reaction, it is also possible to extend to a measurement method in which other molecule, such as nucleic acids (including single chain or double chain DNA, RNA, polynucleotides, oligonucleotides, PNAs (peptide nucleic acids) and the like), saccharides (including oligosaccharides, polysaccharides, sugar chains and the like), and other molecules such as lipids, is subjected to a treatment such as biotinization as necessary by utilizing a similar reaction that occurs between the substance to be measured and the ligand, and using the molecule as a substance to be measured.

(Ligand)

A molecule that can specifically bind to a substance to be measured refers to "ligand". Specifically, a ligand immobilized on the surface of a sensor, which is for capturing the substance to be measured on the surface of the sensor, refers to "solid phase ligand" (if the ligand is an antibody, the ligand refers to "immobilized antibody"), and a ligand that is bind to a fluorescent substance, which is present in a liquid for labeling a substance to be measured, refers to "label ligand" (if the ligand is an antibody, the ligand refers to "labeled antibody"). The ligand parts of the solid phase ligand and label ligand may be the same or different. However, in the case when the solid phase ligand is a polyclonal antibody, the label ligand may be either a monoclonal antibody or a polyclonal antibody, whereas in the case when the solid phase ligand is a monoclonal antibody, it is desirable that the label ligand is a monoclonal antibody or polyclonal antibody that recognizes an epitope that is not recognized by the solid phase ligand.

As the ligand, a suitable ligand may be selected in accordance with the substance to be measured to be captured, and antibodies, receptors, other specific molecules (such as avidin for capturing a biotinylated substance to be measured) and the like, which can specifically bind to a predetermined site of the substance to be measured, can be used as the ligand.

The method for disposing the ligand on the surface of the sensor is not especially limited, and typically, a method such that the functional group possessed by the ligand and the functional group possessed by the SAM-forming molecule (a silane coupling agent or the like) are bonded in accordance with a known means such as an amine coupling process, a thiol coupling process and an indirect capture process (capture process) to thereby connect the ligand to the metal thin film (or a spacer layer) via a SAM-forming molecule. For example, in the amine coupling process, a water-soluble carbodiimide (WSC) such as 1-ethyl-3-(3-dimethylaminopropyl)carbodiimide hydrochloride (EDC) and N-hydroxysuccinic acid imide (NHS) are reacted to activate the carboxyl group of the SAM (the NHS is introduced), and a ligand having an amino group is reacted, whereby the ligand is bonded to the SAM through the NHS.

In addition, in order to prevent the nonspecific adsorption of the substance to be measured, it is preferable to immobilize the above-mentioned ligand on the surface of the sensor to form a solid phase ligand, and then treat the surface of the sensor, the side wall and top panel of the flow path, and the like with a blocking agent such as bovine serum albumin (BSA).

On the other hand, the label ligand can be prepared in a similar manner to that for a complex (conjugate) of a ligand and a fluorescent substance, which is also used in a general immunostaining process. For example, by respectively preparing a complex of a ligand and an avidin (including streptavidin and the like) and a complex of a fluorescent substance and biotin, and reacting these complexes, a complex in which the fluorescent substance is bound to the ligand via the avidin/biotin (four biotins at the maximum can bind to one avidin) can be obtained. Besides the reaction of biotin and avidin as mentioned above, a manner of reaction of a primary antibody—a secondary antibody used in a fluorescence labeling process, or reactions between a carboxyl group and an amino group, between an isothiocyanate and an amino group, between a sulfonyl halide and an amino group, between an iodoacetamide and a thiol group, and the like may also be used.

EXAMPLES

A further specific explanation will be made according to the following experimental examples. The present invention is not construed to be limited to the descriptions of the following experimental examples unless the present invention goes beyond the gist thereof.

Example 1

Immunoassay reactions were conducted with changing the number of times of washing in the first washing step after the primary reaction by selecting the treatment mode. The measurements were conducted in accordance with the flow chart shown in FIG. 1.

A whole blood sample from a healthy person A was prepared, and a part thereof is centrifuged (a trace amount high-speed centrifuge: himac CF15RXII, manufactured by Hitachi Koki Co., Ltd., 1,600 g×15 minutes) to give plasma. Whole blood and plasma samples from the same healthy person, each 100 ul, were each dispensed into a sample well of a reagent cartridge for measuring myoglobin (a cartridge in which various reagents for one immune reaction are filled), the reagent cartridge was then set in a SPFS immunoassay system, and a measurement was initiated. The measurement of the whole blood and the measurement of the plasma were repeatedly measured 6 times, respectively, and CV values (variable factor: the standard deviation/the average of the measured values, unit %) were calculated.

In the case when CV value<10%, the measurement is a measurement with high accuracy and reliability, and the measured value has a clinical value.

The absorbance was measured by irradiating the sample well of the reagent cartridge set in the SPFS immunoassay system with measuring light (constituted by a xenon light source, a spectrometer and a slit) immediately after the initiation of the measurement. The absorbances at a wavelength that has an absorption for a hemocyte hemolystate from human, 540 nm, and a wavelength that does not have an absorption for a hemocyte hemolystate from human, 700 nm, were measured, and in the case when the difference thereof is smaller than a threshold value of 1.0, a reaction was conducted at a normal mode (serum/plasma mode), whereas in the case when the threshold value is 1.0 or more, a reaction was conducted at a whole blood mode with adding the number of times of washing after the primary reaction. The result thereof is shown in Table 1.

In this example, whole blood, serum and sodium heparin plasma were used as samples.

It is understood from Table 1 that, since CV was a low value as 4.2% in this example in which the number of times of washing after the primary reaction was added in treating the whole blood, a sufficiently stable measuring was conducted.

Comparative Example 1

In Comparative Example 1, whole blood was forcedly treated under a normal mode condition. The result thereof is shown in Table 1.

It was found that, in the case when the whole blood was treated at a normal mode, since the measured mean value was a low value and CV was a high value as 13.0%, and thus the washing of the whole blood was insufficient and thus a stable measurement was not able to be conducted.

TABLE 1

|  | Sample | 540 nm OD | 700 nm OD | Treatment mode | Number of times after primary reaction | Number of times of repetitive measurements | Measured average value (ng/ml) | CV value (%) |
|---|---|---|---|---|---|---|---|---|
| Example 1 | Whole blood | 3.056 | 1.013 | Whole blood mode | 5 | 6 | 53.4 | 4.2 |
|  | Blood serum | 0.109 | 0.073 | Normal mode | 3 | 6 | 55.8 | 3.8 |
|  | Heparin sodium plasma | 0.034 | 0.028 | Normal mode | 3 | 6 | 57.3 | 5.6 |
|  | Heparin lithium plasma | 0.043 | 0.027 | Normal mode | 3 | 6 | 56.1 | 4.7 |
| Comparative Example 1 | Whole blood | 3.075 | 0.958 | Normal mode | 3 | 6 | 43.8 | 13.0 |

Example 2

An immunoassay reaction was conducted with changing the dilution rate of the sample to be two times of that of a general sample by selecting the treatment mode. The measurement was conducted in accordance with the flow chart shown in FIG. 2.

A whole blood sample from a healthy person B was prepared, and a part thereof was centrifuged (a trace amount high-speed centrifuge: himac CF15RXII, manufactured by Hitachi Koki Co., Ltd., 1,600 g×15 minutes) to give plasma. In this SPFS immunoassay system, in the case of a normal mode treat, the sample and diluted liquid were mixed at 1:1 in the apparatus, and the immune reaction was conducted by using a 2-times diluted liquid. In this example, 4-times dilution of the sample was realized by changing the mixing ratio of the sample and diluted liquid in the apparatus. In a similar manner to that of Example 1, the myoglobin concentrations of the whole blood and plasma samples from the same healthy person were repeatedly measured 6 times by a SPFS immunoassay system by a treatment mode switching standard. The result thereof is shown in Table 2.

It is understood from Table 2 that CV was 7.2%, which was a low value of 10% or less, in treating the whole blood, in this example in which the dilution rate of the sample was higher than that in the normal mode, and thus a sufficiently stable measuring was conducted.

Example 3

The measuring was conducted in a similar manner to that of Example 2, except that the dilution rate of the sample was changed to be 3 times of a general sample, and the sample was diluted by 6-times, by selecting the treatment mode. The result thereof is shown in Table 3.

It is understood from Table 3 that CV was 5.0%, which was a low value of 10% or less, in treating the whole blood, in this example in which the dilution rate of the sample was higher than that of the normal mode, and thus a sufficiently stable measuring was conducted.

Comparative Example 2

In Comparative Example 2, whole blood was forcedly treated under a normal mode condition. The result is shown in Tables 2 and 3. In the case when the whole blood was treated at a normal mode, the measured mean value was a low value, and CV was a high value as 15.7%. Therefore, it was found that, since the dilution of the whole blood was insufficient, a stable measuring was not able to be conducted.

TABLE 2

|  | Sample | 540 nm OD | 700 nm OD | Treatment mode | Dilution rate | Number of times of repetitive measurements | Measured average value (ng/ml) | CV value (%) |
| --- | --- | --- | --- | --- | --- | --- | --- | --- |
| Example 2 | Whole blood | 3.018 | 1.047 | Whole blood mode | 4 | 6 | 28.9 | 7.2 |
|  | Heparin sodium plasma | 0.038 | 0.022 | Normal mode | 2 | 6 | 30.8 | 4.9 |
|  | Heparin lithium plasma | 0.034 | 0.028 | Normal mode | 2 | 6 | 28.1 | 3.8 |
| Comparative Example 2 | Whole blood | 3.029 | 1.017 | Normal mode | 2 | 6 | 25.3 | 15.7 |

TABLE 3

|  | Sample | 540 nm OD | 700 nm OD | Treatment mode | Dilution rate | Number of times of repetitive measurements | Measured average value (ng/ml) | CV value (%) |
| --- | --- | --- | --- | --- | --- | --- | --- | --- |
| Example 3 | Whole blood | 3.031 | 1.023 | Whole blood mode | 6 | 6 | 26.7 | 5.0 |
|  | Heparin sodium plasma | 0.038 | 0.022 | Normal mode | 2 | 6 | 30.8 | 4.9 |
|  | Heparin lithium plasma | 0.034 | 0.028 | Normal mode | 2 | 6 | 28.1 | 3.8 |
| Comparative Example 2 | Whole blood | 3.029 | 1.017 | Normal mode | 2 | 6 | 25.3 | 15.7 |

In this embodiment, an example in which modes were isolated into two treatment modes of "whole blood mode" and "normal mode (serum/plasma mode)", but as a matter of course, it is also possible to isolate the treatment mode into not only these two modes but also three or more mode in accordance with absorbance, and to set the treatment condition to different treatment conditions of multisteps.

The invention claimed is:

1. An immunoassay method utilizing surface plasmon, comprising:
   an absorbance measurement step of measuring an absorbance of a sample,
   a mode setting step of classifying the sample type of the sample according to the result of the absorbance measured in the absorbance measurement step, wherein the mode is a mode for a whole blood sample and a mode for a serum sample or a plasma sample,
   a treatment condition setting step of setting a treatment condition according to the mode of the sample set in the mode setting step, for treating the sample in one or more reaction step(s) thereafter,
   wherein a primary reaction step of the one or more reaction steps comprises forming a complex between a substance to be measured in the sample and a ligand, and
   a surface plasmon measurement step for qualitatively or quantitatively analyzing the substance to be measured in the sample on a sensor substrate.

2. The immunoassay utilizing surface plasmon according to claim 1, wherein the treatment condition is a number of times of washing in a washing step that is conducted after the primary reaction step, and, in the case when a labeling reaction step is conducted, before the labeling reaction step.

3. The immunoassay utilizing surface plasmon according to claim 1, wherein the treatment condition is a dilution rate of a sample in a dilution step.

4. The immunoassay utilizing surface plasmon according to claim 1, wherein the treatment condition is a time for the primary reaction step.

5. The immunoassay utilizing surface plasmon according to claim 2, wherein the mode setting step is a step of setting a whole blood mode for a whole blood sample and a normal mode for a serum sample or a plasma sample, and the number of times of washing for the whole blood mode is more than that for the normal mode.

6. The immunoassay utilizing surface plasmon according to claim 3, wherein the mode setting step is a step of setting a whole blood mode for a whole blood sample and a normal mode for a serum sample or a plasma sample, and the dilution rate for the whole blood mode is higher than that for the normal mode.

7. The immunoassay utilizing surface plasmon according to claim 4, wherein the mode setting step is a step of setting the first mode of the sample as a whole blood mode for a whole blood sample and the second mode as a normal mode for a serum sample or a plasma sample, and the time for the primary reaction step in the whole blood mode is longer than that for the normal mode.

8. The immunoassay utilizing surface plasmon according to claim 1, which is an immunoassay utilizing surface plasmon-field enhanced fluorescence spectroscopy.

9. An immunoassay system utilizing surface plasmon, wherein the immunoassay according to claim 1 is conducted.

10. The immunoassay utilizing surface plasmon according to claim 2, wherein the treatment condition is a dilution rate of a sample in a dilution step.

11. The immunoassay utilizing surface plasmon according to claim 2, wherein the treatment condition is a time for the primary reaction step.

12. The immunoassay utilizing surface plasmon according to claim 1, which is an immunoassay utilizing surface plasmon-field enhanced fluorescence spectroscopy.

13. An immunoassay system utilizing surface plasmon, wherein the immunoassay according to claim 1 is conducted.

14. The immunoassay utilizing surface plasmon according to claim 3, wherein the treatment condition is a time for the primary reaction step.

15. The immunoassay utilizing surface plasmon according to claim 2, which is an immunoassay utilizing surface plasmon-field enhanced fluorescence spectroscopy.

16. An immunoassay system utilizing surface plasmon, wherein the immunoassay according to claim 2 is conducted.

* * * * *